United States Patent [19]

Northrup, III et al.

[11] Patent Number: 5,961,539
[45] Date of Patent: Oct. 5, 1999

[54] METHOD AND APPARATUS FOR SIZING, STABILIZING AND/OR REDUCING THE CIRCUMFERENCE OF AN ANATOMICAL STRUCTURE

[75] Inventors: William F. Northrup, III; Joanne B. Northrup, both of Edina, Minn.

[73] Assignee: Segmed, Inc., Edina, Minn.

[21] Appl. No.: 08/786,892

[22] Filed: Jan. 17, 1997

[51] Int. Cl.⁶ ................................................. A61B 17/00
[52] U.S. Cl. ........................................... 606/232; 606/148
[58] Field of Search .................................... 606/148, 139, 606/144, 232; 623/2

[56] References Cited

U.S. PATENT DOCUMENTS

| | | |
|---|---|---|
| 4,042,979 | 8/1977 | Angell . |
| 4,217,665 | 8/1980 | Bex et al. . |
| 4,275,736 | 6/1981 | Chodorow et al. . |
| 4,489,446 | 12/1984 | Reed . |
| 4,637,380 | 1/1987 | Orejola . |
| 4,676,245 | 6/1987 | Fukuda . |
| 4,823,794 | 4/1989 | Pierce . |
| 4,917,698 | 4/1990 | Carpentier et al. . |
| 5,011,481 | 4/1991 | Myers et al. ................................ 623/2 |
| 5,041,130 | 8/1991 | Cosgrove et al. . |
| 5,061,277 | 10/1991 | Carpentier et al. . |
| 5,064,431 | 11/1991 | Gilbertson et al. . |
| 5,089,008 | 2/1992 | Chen . |
| 5,104,407 | 4/1992 | Lam et al. . |
| 5,163,943 | 11/1992 | Mohiuddin et al. . |
| 5,201,880 | 4/1993 | Wright et al. . |
| 5,219,359 | 6/1993 | McQuilkin et al. . |
| 5,258,021 | 11/1993 | Duran . |
| 5,263,973 | 11/1993 | Cook . |
| 5,306,301 | 4/1994 | Graf et al. . |
| 5,366,480 | 11/1994 | Corriveau et al. . |
| 5,468,242 | 11/1995 | Reisberg . |
| 5,549,631 | 8/1996 | Bonutti . |
| 5,709,695 | 1/1998 | Northrup, III ........................... 606/148 |

FOREIGN PATENT DOCUMENTS

| | | |
|---|---|---|
| 1335260 | 9/1987 | U.S.S.R. . |
| 2 063 675 | 6/1991 | United Kingdom . |
| WO 95/06447 | 3/1995 | WIPO . |

OTHER PUBLICATIONS

Product Pamphlet "Prosthetic Rings and Accessories for Tricuspid and Mitral Valvuloplasty," American Edwards Laboratories, Dec., 1985.

Van Rijk – Zwikker, et al., "Mitral Valve Anatomy and Morphology: Relevance to Mitral Valve Repalcement and Valve Reconstruction," J. Card. Surg., 1994; 9 (Suppl): 255–261.

*Primary Examiner*—Michael Buiz
*Assistant Examiner*—Kevin Truong
*Attorney, Agent, or Firm*—Patterson & Keough, P.A.

[57] ABSTRACT

An annuloplasty system is disclosed that respects the uniqueness of each anterior mitral or tricuspid valve leaflet as the appropriate template for an annuloplasty ring. Each dilated tissue annulus is brought to a precise anterior mitral or tricuspid leaflet perimeter dimension, rather than to the dimension of a specific-sized annuloplasty ring. Thus, precise measured plication of the dilated mitral or tricuspid annulus is possible in every case, resulting in mitral or tricuspid repair with greater predictability and reproduceability. Substantially rigid suture support segments to be placed at least partially circumferentially about an anatomical structure, such as a heart valve, are delivered to the heart valve by a plurality of linked-together segment holders. The segment holders also function as sizing elements for precisely and easily measuring the perimeter of an anterior mitral or tricuspid leaflet, for example. The segments are enclosed in a double layer of autologous viable pericardium, according to one embodiment, forming a pericardial tube. Together, the pericardial tube and the segments create an annuloplasty ring presenting significant advantages over the prior art. Devices and methods according to the invention can also be used to size, stabilize, and/or reduce the circumference of other anatomical structures, not just mitral and tricuspid valves.

40 Claims, 8 Drawing Sheets

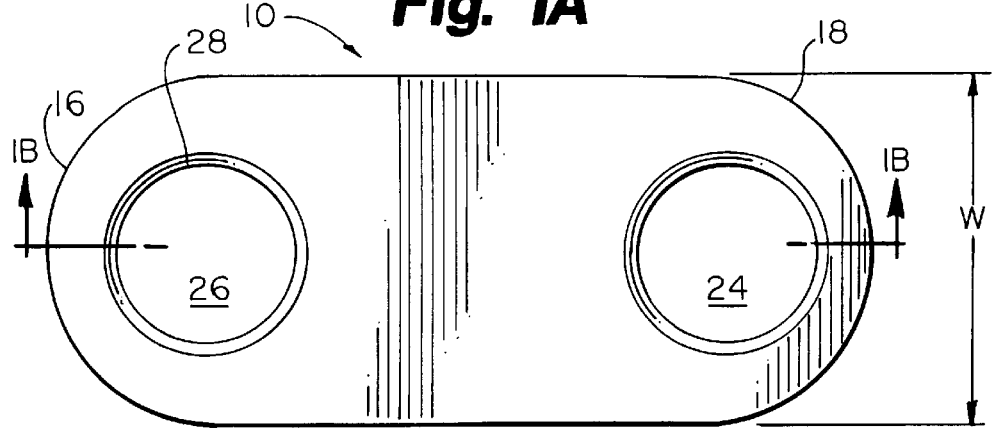
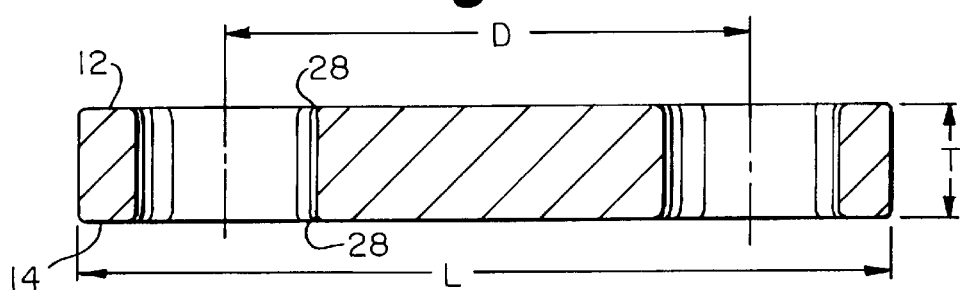
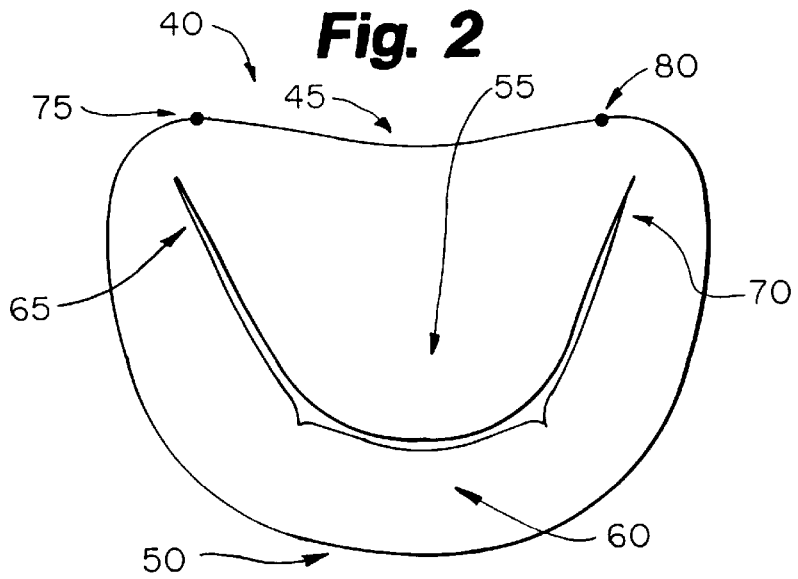

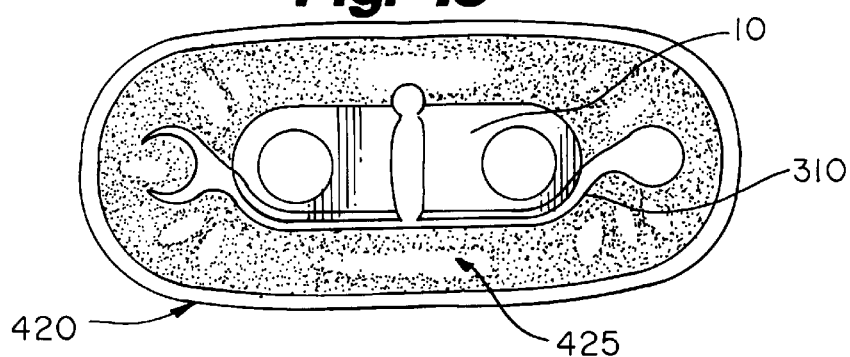
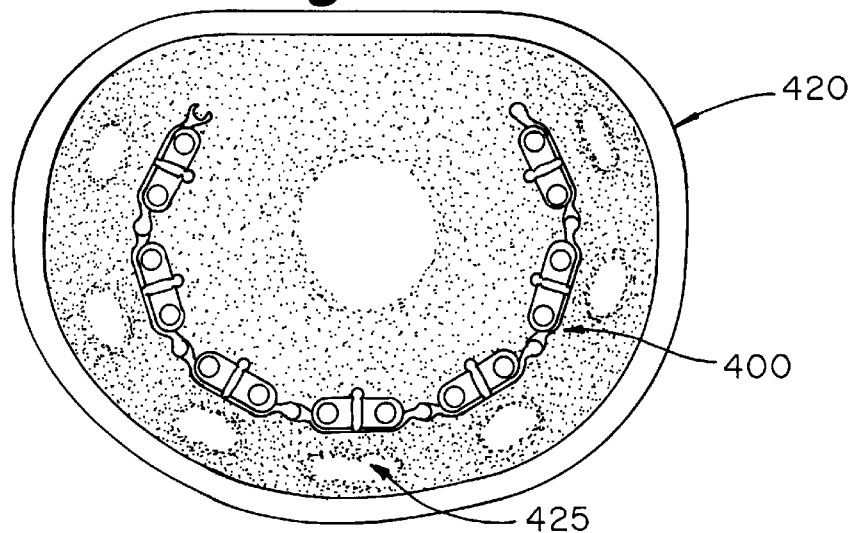
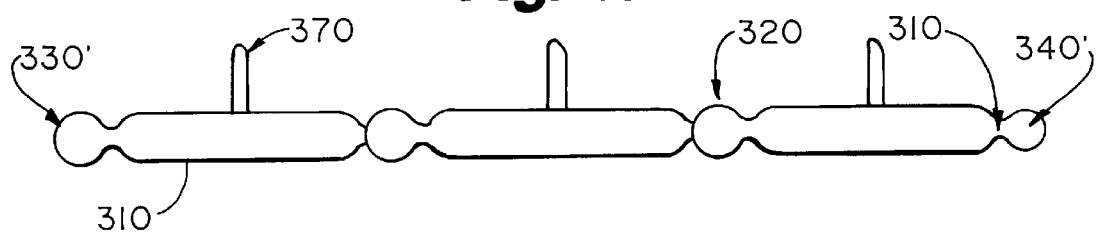
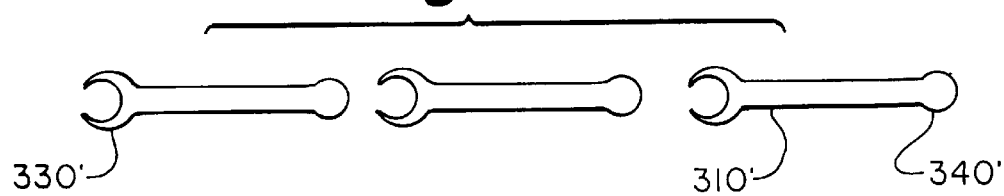

METHOD AND APPARATUS FOR SIZING, STABILIZING AND/OR REDUCING THE CIRCUMFERENCE OF AN ANATOMICAL STRUCTURE

CROSS-REFERENCE TO RELATED APPLICATIONS

The subject matter of this application is related to the subject matter of the following U.S. patent applications, all of which are incorporated by reference herein:

U.S. patent application Ser. No. 08/288,124 to Northrup, now U.S. Pat. No. 5,593,424, issued Jan. 14, 1997;

U.S. patent application Ser. No. 08/705,179 to Northrup, now U.S. Pat. No. 5,709,695, issue Jan. 20, 1998; and U.S. Provisional Patent Application No. 60/024,103 to Northrup, pending, priority to which is claimed under 35 U.S.C. § 119(e).

BACKGROUND OF THE INVENTION

1. Field of the Invention

The invention relates generally to devices and methods for sizing, stabilizing and/or reducing the circumference of an anatomical structure, such as a heart valve, and more particularly, to such devices and methods that can also deliver certain suture support elements to the anatomical structure with a consistent, uniform, predetermined spacing.

2. Description of Related Art

Although current artificial and prosthetic heart valves can greatly improve the condition of a patient, these devices present serious drawbacks, such as thrombogenicity (tendency towards thrombus formation and subsequent detachment with embolization) and limited durability secondary to tissue structure failure, i.e. SVD (structural valve deterioration).

Other complications can also occur, such as noise, interference with hemodynamics, especially in smaller sizes, hemolysis (destruction of blood elements), endocarditis (valve infection) and dehiscence of the valve. Because of the risk of embolism, the majority of patients who receive mechanical artificial heart valves must take anticoagulant medication for life, with the concomitant risk of hemorrhage and necessary change in lifestyle. Patients who receive tissue bioprostheses and commercially available annuloplasty rings generally must take anticoagulative medication for about three months.

Different and more recent developments in the field of cardiac surgery have included attempts to surgically repair, instead of replace, diseased heart valves and other vascular tissue. A variety of surgical maneuvers and procedures exist for this purpose. Many cardiac surgeons consider this type of reconstructive surgery superior to valve replacement in many respects, although it is generally more technically difficult and time-consuming to perform and not always possible in every patient.

Among the variety of reconstructive surgical procedures, valve annuloplasty is the most frequently performed in the tricuspid and mitral valves. A valve annuloplasty procedure selectively reduces the size of a dilatated valve annulus. A number of prosthetic rings exist for this purpose, such as the commercially available Carpentier ring (distributed by American Edwards Laboratories).

The Carpentier method of valvuloplasty employing the Carpentier ring is disclosed in the product pamphlet "Prosthetic Rings and Accessories for Tricuspid and Mitral Valvuloplasty", produced by American Edwards Laboratories in December, 1985. See also U.S. Pat. Nos. 5,061,277 and 4,917,698 to Carpentier for related discussions.

Commercially available annuloplasty rings have a number of drawbacks. First, they are expensive. Second, unless they are either rigid or sutured to the tissue annulus while still attached to a rigid holder, they may suffer an unpredictable degree of longitudinal shortening within the confines of each mattress suture used to secure the ring to the tissue annulus. (Even a running suture preferred by a few surgeons is still likely to produce some longitudinal shortening of the ring.) Thus, they may fail to provide a precise, predictable, reproducible annuloplasty. Further, without a rigid element present when the suture is tied, each suture is necessarily tied with variable and unpredictable degrees of tension by the operating surgeon.

Third, most annuloplasty rings are completely circumferential, committing the operating surgeon to placing sutures in the anterior annulus where dilatation rarely occurs and where a tissue tear from inexact suture placement can produce a hole in the aortic-mitral curtain, resulting in significant mitral regurgitation. Fourth, a rigid mitral ring, because it is pre-shaped to an oval configuration, must be precisely placed and is not very forgiving with inexact placement. Fifth, a rigid tricuspid ring can dehisce if not made to conform to the slightly spiral, nonplanar shape of the tissue annulus. Sixth, any rigid ring impedes the normal flexibility of the tissue annulus during ventricular contraction. Seventh, all commercially available rings, which generally come only in a few generic sizes and shapes, are necessarily approximations of the exact size and shape of the original mitral valve orifice and therefore are usually not truly precise. Finally, ring implantation with conventional surgical technique is a significantly invasive procedure.

A need exists, therefore, for an apparatus and method which provide a customized annuloplasty, tailored to the needs of the original size and shape of each unique mitral, tricuspid, or other orifice and of specific pathophysiological situations, including but not limited to a limited annuloplasty of any valve annulus, a subtotal annuloplasty of any valve, or a complete annuloplasty of any valve annulus. A need also exists for an apparatus and method which allow the repaired vascular structure to retain its flexibility in all planes while preventing further dilatation or circumferential lengthening of the tissue annulus or vascular structure. Additionally, a need exists for an apparatus and method that are precise, customizable, simple to use and manufacture, low-cost, and, as needed, minimally invasive.

SUMMARY OF THE INVENTION

To meet the above and other needs, embodiments of the invention provide a sizing and delivery system for use in a surgical procedure on an anatomical structure, for example on a heart valve of a patient. The sizing and delivery system preferably includes segment means, for reducing the circumference of the heart valve, or stabilizing the circumference as needed. The segment means includes a plurality of preferably substantially identical suture support segments, the suture support segments having apertures therethrough for receiving the sutures. The segments preferably are constructed for placement at least partially circumferentially about the heart valve annulus, forming a line of discrete suture support segments that can reduce the circumference of the valve annulus by plicating tissue underneath and/or between the individual segments.

The sizing and delivery system further includes segment holding means for releasably holding the segment means during delivery to the heart valve or other anatomical structure during the surgical procedure. The segment holding means preferably includes a plurality of preferably substantially identical segment holders, each of which includes linking means for connecting adjacent segment holders together. The linking means, for example a plurality of universal ball-and-socket joints, provides flexibility in a number of planes while maintaining a desired overall shape, and preferably in all planes.

According to a preferred embodiment, a desired number of the segment holders can be linked together to form a line of linked segment holders of a desired length, corresponding to the unique size and/or shape of a heart valve, or heart valve portion, e.g. the perimeter dimension of the anterior mitral or tricuspid leaflet, of the individual patient. The segment holders preferably are each of known, substantially identical lengths to allow precise valve sizing. Further, the segment holders preferably maintain each suture support segment a known distance from an adjacent support segment, creating uniform intervals for implantation of the support segments.

The system preferably further includes belt means for readily releasably securing the segment means to the segment holding means. The belt means preferably comprises separation notch means for allowing the belt means to be readily severed, releasing the segment means from the segment holding means. Additionally, clamp fins can be provided, each clamp fin being constructed for ready grasping by a clamp or other instrument to allow easy relocation of the segment holders and thus the suture support segments themselves.

According to additional embodiments, the invention can be used purely as a sizing system, in which the segment holders are used as sizing elements, purely as a delivery system for delivering the suture support segments, or as both a sizing and a delivery system.

Finally, embodiments of the invention can be used in minimally invasive surgical procedures, representing a significant advantage over prior art annuloplasty rings. For example, the individual segments and/or segment holders can be fed one-by-one through an incision of minimal size such as "port-access" for delivery to a heart valve.

Other important aspects of the invention in its various embodiments will become apparent from the following Detailed Description of Preferred Embodiments.

BRIEF DESCRIPTION OF THE DRAWINGS

Preferred embodiments of the invention will be described with respect to the figures, in which like reference numerals denote like elements and in which:

FIG. 1A is a top view of a suture support segment according to an embodiment of the invention;

FIG. 1B is a cross-sectional view along line 1B–1B of FIG. 1A;

FIG. 2 is a view of a normal closed mitral heart valve;

FIGS. 15–16 are top views showing packaging arrangements for a sizing and delivery system, according to an embodiment of the invention;

FIG. 17 is a side view of a sizing system according to an embodiment of the invention; and FIG. 18 is a top view of the FIG. 17 system.

DETAILED DESCRIPTION OF PREFERRED EMBODIMENTS

Figure 3:
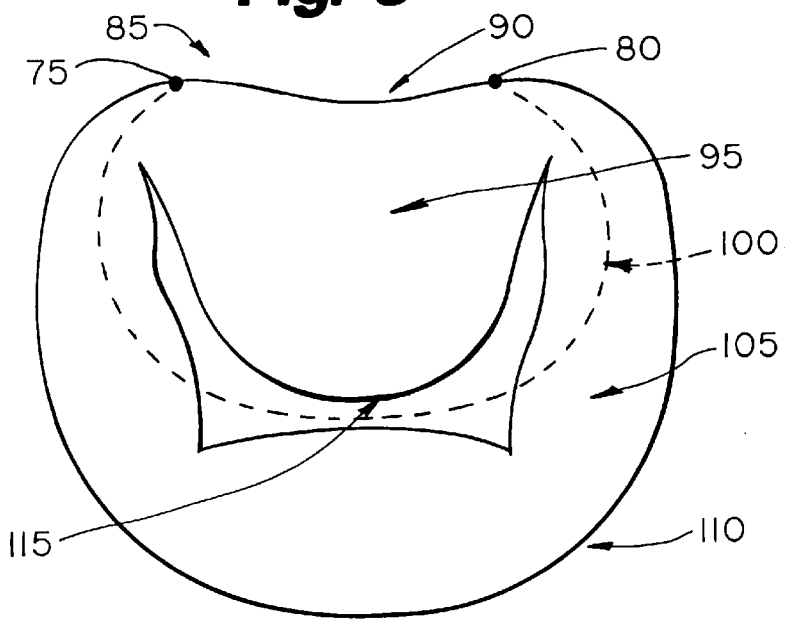
FIG. 3 is a view of a typical posterior mitral annulus dilatation.

Embodiments of the present invention provide a number of advantages over other devices and methods for stabilizing and/or reducing the circumference of an anatomical structure, such as annuloplasty rings. Embodiments of the invention, for example, provide extreme precision in effecting repair of a mitral or tricuspid heart valve. The anterior mitral or tricuspid valve leaflet is recognized as a unique, advantageous template for repairing a dilated tissue annulus. Each dilated tissue annulus is brought to a precise anterior mitral or tricuspid leaflet perimeter dimension, rather than to the dimension of a specific-size annuloplasty ring, which itself is an approximation or "best fit" with the anterior leaflet. Surgeons are thus encouraged to begin with the exact perimeter dimension of each unique, unfurled anterior leaflet size and shape particular to a specific patient. Embodiments of the invention allow for an absolutely precise measured plication of the dilated annulus in every case, and allow for absolute precision and accuracy in the measurement of the linear dimension of the annuloplasty ring-equivalent material. This results in valve repair with greater predictability and reproduceability, impossible with any of the currently available annuloplasty rings for every unique case.

The customizability of the invention appeals to the artistry and creativity of the individual surgeon. Annuloplasty rings of appropriate length can be created in all cases, even with an anterior mitral or tricuspid leaflet of unusual size and/or shape. Either biological or non-biological material can be used to form the annuloplasty ring itself, according to embodiments of the invention, and either a partial or complete annuloplasty ring can be created. Additionally, alternative templates, other than the anterior mitral or tricuspid leaflet, readily can be used.

Embodiments of the invention also present significant advantages because of their simplicity in design, manufacture and use. Embodiments of the invention allow hospital inventories to stock only one size segment, since one size can be used to fit all cases. Additionally, hospital inventories do not require separate sizers of various dimensions, since the segment delivery system is also a disposable universal sizer. Further, no inventories of ring material will be necessary if untreated, viable autologous pericardium, or other suitable material, is available and acceptable.

Embodiments of the invention also provide a host of other advantages. These advantages include:

A remodeling annuloplasty can be accomplished without involving the anterior mitral or septal tricuspid annulus, in most cases.

Normal geometry and physiology of the mitral or tricuspid apparatus can be maintained, with 3-dimensional flexibility during the cardiac cycle. Contractility of the mitral or tricuspid apparatus is preserved.

Optimal surface area of the mitral or tricuspid orifice is conserved.

Compatibility with any pathological condition requiring annuloplasty is allowed.

Stresses on sutures are reduced, by maintaining flexibility throughout the cardiac cycle.

An optimal relationship between the ring orifice area and the amount of valvular tissue is allowed, preventing left ventricular outflow tract obstruction.

Fixation of the diastolic dimension of the mitral or tricuspid annulus is allowed, while preserving its normal, flexible contour.

Embodiments of the invention reduce the circumference of an anatomical structure by promoting tissue plication in precise regions. Alternatively, in non-plicating embodiments, embodiments of the invention can be used merely to stabilize the circumference of such anatomical structures, preventing dilatation or other abnormality. Embodiments of the invention have particular application to vascular structures, such as mitral or tricuspid heart valves, but the invention is by no means limited to these embodiments. A wide variety of other anatomical structures can also be repaired according to embodiments of the invention.

Turning to the figures, a basic aspect of the invention involves a plurality of suture support segments, like that shown generally at 10 in FIGS 1A–1B. Each individual suture support segment 10 includes upper surface 12, lower surface 14, and opposite sides 16, 18. Two suture holes or apertures 24, 26 extend through suture support segment 10. Each suture aperture 24, 26 preferably includes chamfered portions 28 at upper surface 12 and lower surface 14 of segment 10, to reduce abrasion and consequent fraying or other damage to sutures passing through the apertures 24, 26. Apertures 24, 26 also preferably include substantially straight sidewalls as shown, and preferably are large enough to accommodate a 2-0 suture and swedged-on needle. Of course, other aperture and sidewall shapes and configurations are also contemplated, although the illustrated features have been found to be optimal. Further, although suture support segment 10 may be of any suitable overall shape, the rounded-end rectangle shape shown in FIGS. 1A–1B is particularly desirable.

Suture apertures 24, 26 are separated by a center-to-center distance D, which preferably is about 5.0 mm ±3.0 mm. Segment 10 preferably has a width W of about 3.0 mm ±1.0 mm, a thickness T of about 1.0 mm, and a length L of about 7.0 mm. Of course, other dimensions to fit a particular surgical application are also contemplated.

Suture support segment 10 can be made of any suitable material that is preferably inert, non-corrosive, non-thrombogenic and biocompatible with blood and tissue. A material already approved by the FDA for intra-vascular use is preferred, such as titanium, or an alloy of titanium such as a medical-grade titanium-aluminum-vanadium alloy.

Suture support segment 10 should be non-deformable in its long axis, and therefore substantially rigid. Each suture support segment 10 preferably accommodates a single horizontal mattress suture incorporating a portion of the circumference of a tissue annulus beneath it.

As will be described, multiple segments 10 are appropriately spaced and then covered with a flexible material, such as autologous pericardium, to create an annuloplasty ring. The dilated tissue annulus of e.g. a mitral or tricuspid heart valve can be precisely plicated to an exact dimension of several, individual segments 10, with consistent intervals defined between segments 10 and a specific length of flexible ring material. The annuloplasty ring can be either partial or complete, and has overall flexibility. As will become apparent, the disclosed system combines the best features of currently available rigid and flexible annuloplasty rings and takes valve repair to a higher level of precision and efficiency than previously possible.

According to a preferred embodiment of the invention, it is assumed that a posterior mitral annuloplasty alone, but which incorporates both fibrous trigones, is sufficient to achieve adequate remodeling in virtually all cases of mitral annular dilatation. The posterior annulus is simply restored to its original perimeter dimension. It is also assumed that this original posterior annulus dimension is substantially identical to the perimeter dimension of the free margin of the anterior mitral or tricuspid leaflet.

Placement and use of a sizing and delivery system according to embodiments of the invention will now be described, with respect to a heart valve repair procedure.

FIG. 2 shows a normal closed mitral valve 40, with anterior annulus 45, posterior annulus 50, anterior leaflet 55, and posterior leaflet 60. Leaflets 55, 60 define anterior and posterior commissures 65, 70. Normal mitral valve 40 also includes fibrous anterior and posterior trigones 75, 80.

FIG. 3 shows a diseased mitral valve 85. Although anterior annulus 90 between trigones 75, 80 generally is unaffected, as is anterior leaflet 95, posterior leaflet 105 and posterior annulus 110 are posterially displaced from their normal positions. The original location of displaced posterior annulus 110, for example, is illustrated in dashed lines at 100. This posterior displacement reduces the coaptation surface area of anterior leaflet 95 and posterior leaflet 105 as shown at 115, impairing optimal valve function.

Figure 4:
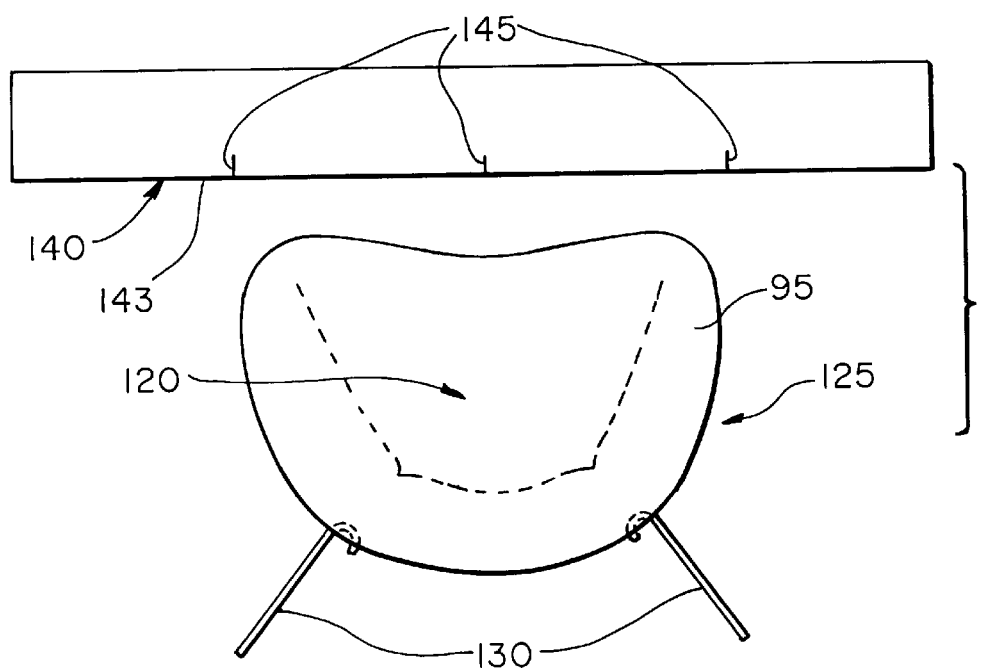
FIG. 4 is a view of an unfurled anterior mitral leaflet and a pericardial strip, according to an embodiment of the invention.

As shown in FIG. 4, anterior mitral leaflet 95 is unfurled, using nerve hooks 130 or other means, to substantially cover mitral orifice 120. The unique unfurled anterior mitral leaflet perimeter dimension 125 of the particular patient is then determined. That dimension will then serve as a precise template for the annuloplasty ring, which can be either a completely or partially circumferential ring depending on the specific pathology and/or surgeon preference. A preferred method and apparatus for determining perimeter dimension 125 will be described with respect to FIGS. 11–16, below.

A strip 140 of ring material is then laid out at an anterior side of mitral orifice 120, as shown in FIG. 4. Strip 140 corresponds to the precise length of the anterior mitral leaflet perimeter dimension, with some extra material left at the ends as will be described. Additionally, strip 140 is preferably slightly more than twice the width needed to cover segments 10.

As mentioned above, viable, autologous pericardium, ideally from the same patient, is the preferred material for strip 140. Such pericardium creates the lowest profile with the least amount of foreign material of any available annuloplasty ring. It "melts" into the tissue annulus, becoming virtually indistinguishable from it. It is unlikely to stiffen with time, as has been reported with other flexible annuloplasty rings, or to shrink or stretch. It minimizes scar and pannus formation, eliminating the need for tissue ingrowth, especially when used as a pericardial tube as described below. Further, when used as a pericardial tube, non-thrombogenicity can be virtually guaranteed and the need for any Warfarin anticoagulation eliminated. Of course, other biological or non-biological ring materials can also be used, such as DACRON or another suitable fabric.

Pericardial strip 140 is placed shiny-side-down on a suitable surface, such as a flat towel. It is then held taut at the four corners well above the retractor on the anterior side of mitral orifice 120. Near posterior edge 143 of strip 140, a marking pen, suture or other suitable means is used to designate at 145 the end and middle (and the ¼ and ¾ points) of the final longitudinal dimension, creating two or four quadrants to facilitate easy suture placement.

Figure 5:
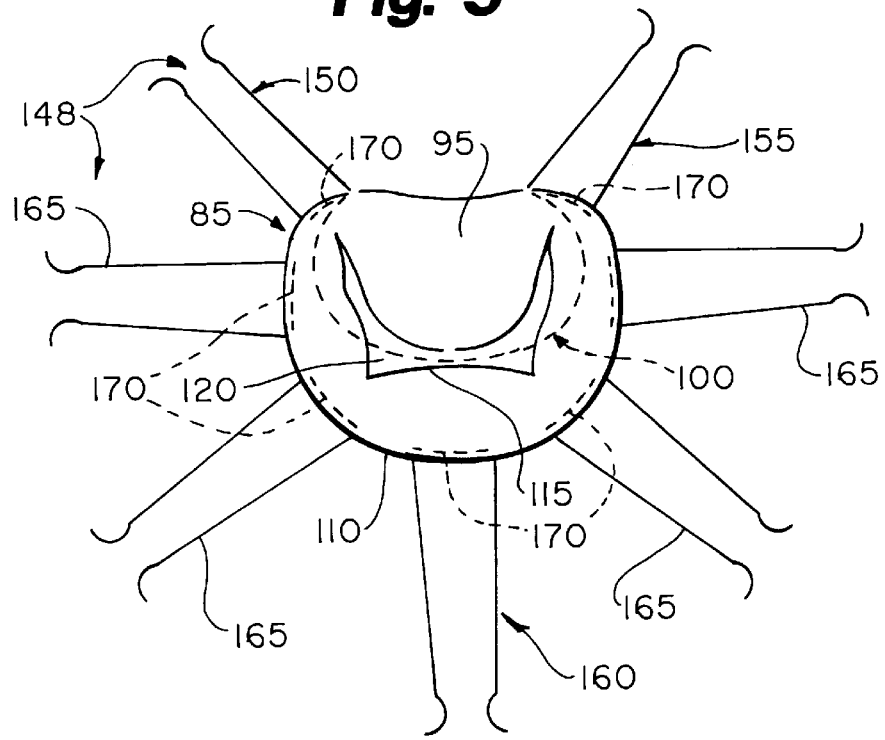
FIG. 5 is a view showing suture placement in a tissue annulus, according to an embodiment of the invention.

Then, turning to FIG. 5, sutures 148 are properly placed in the posterior tissue annulus 110 of diseased mitral valve 85, preferably with even spacing. Sutures 148 in the illustrated embodiment include anterior trigone/commissure plicating mattress suture 150, posterior trigone/commissure plicating mattress suture 155, middle posterior annulus plicating mattress suture 160, and remaining mattress sutures 165. Although evenly spaced mattress sutures are highly preferred, and according to one embodiment 2-0 braided polyester mattress sutures are used, of course other suitable suture types are contemplated according to the invention.

Figure 6:
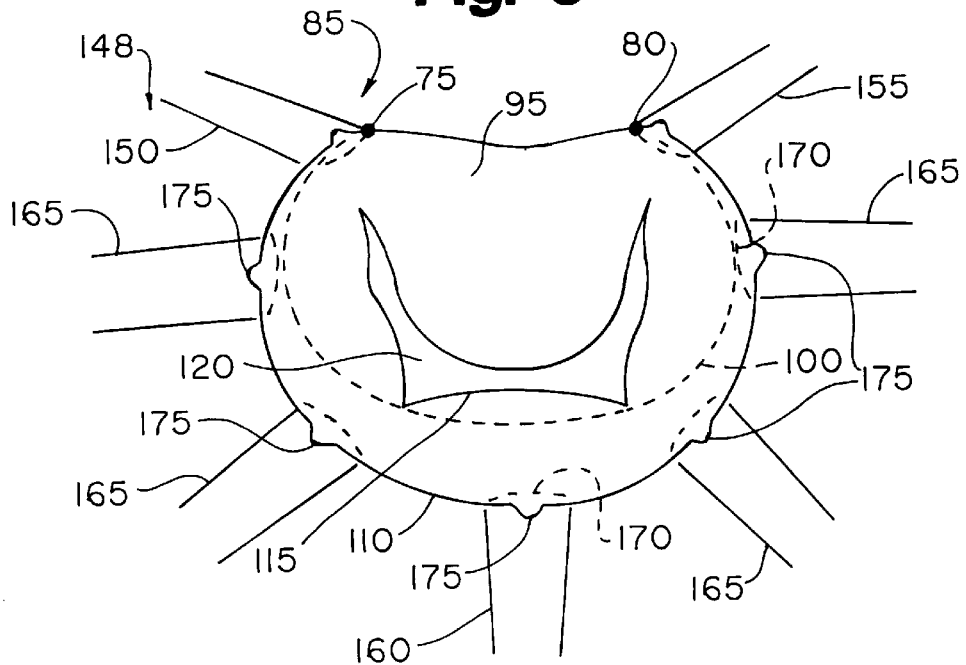
FIG. 6 is a view showing traction on mattress sutures producing partial annulus plication, according to an embodiment of the invention.

The first sutures to be placed are those in the vicinity of the anterior and posterior commissures, that is, sutures 150, 155, according to a preferred embodiment. The medial limbs of these sutures preferably intersect trigones 75, 80, as shown in FIG. 6. Sutures 150, 155 preferably are then laid out radially from mitral orifice 120.

Next, the exact middle of posterior annulus 110 is found, and middle posterior suture 160 is placed if an odd number of segments 10 are called for. If an even number of sutures is called for, on the other hand, a marking suture or a mark with a pen can be placed to mark the middle of posterior annulus 110. The remaining plicating mattress sutures 165 needed within the remaining quadrants are placed using a "divide and conquer" method. The total number of plicating mattress sutures 148 corresponds to the number of segments 10 determined from the anterior mitral leaflet measurement, not to the degree of dilatation of the posterior mitral annulus 110, as explained above.

Although seven sutures 148 are illustrated in the FIG. 5 embodiment, the exact number of sutures will depend on the length of autologous pericardial strip 140, that is, on perimeter dimension 125 of anterior mitral leaflet 95. The specific number of sutures will match the specific number of segments 10 needed, based on perimeter dimension 125. Preferred embodiments for precisely determining the exact number of segments needed will be described with respect to FIGS. 11–16.

For posterior annuloplasty, all sutures 148 must purposely plicate annular tissue within the two limbs of each mattress suture loop, as illustrated at 170 in FIGS. 5 and 6. The exact amount of plication is determined by the specific length of tissue annulus traversed by the suture loop. For anterior annuloplasty, on the other hand, suture loops in anterior annulus 90 must purposely avoid plication, by traversing a specific length of tissue annulus 90 that exactly corresponds to the interval between suture apertures 24, 26 in segment 10.

Once sutures 148 are properly placed, all of sutures 148 are pulled up, effecting an overall plication of tissue annulus 110 with simple traction. Plication of tissue annulus 110 within the two limbs of each mattress suture 148 is represented at 175 in FIG. 6, for example.

Figure 7:
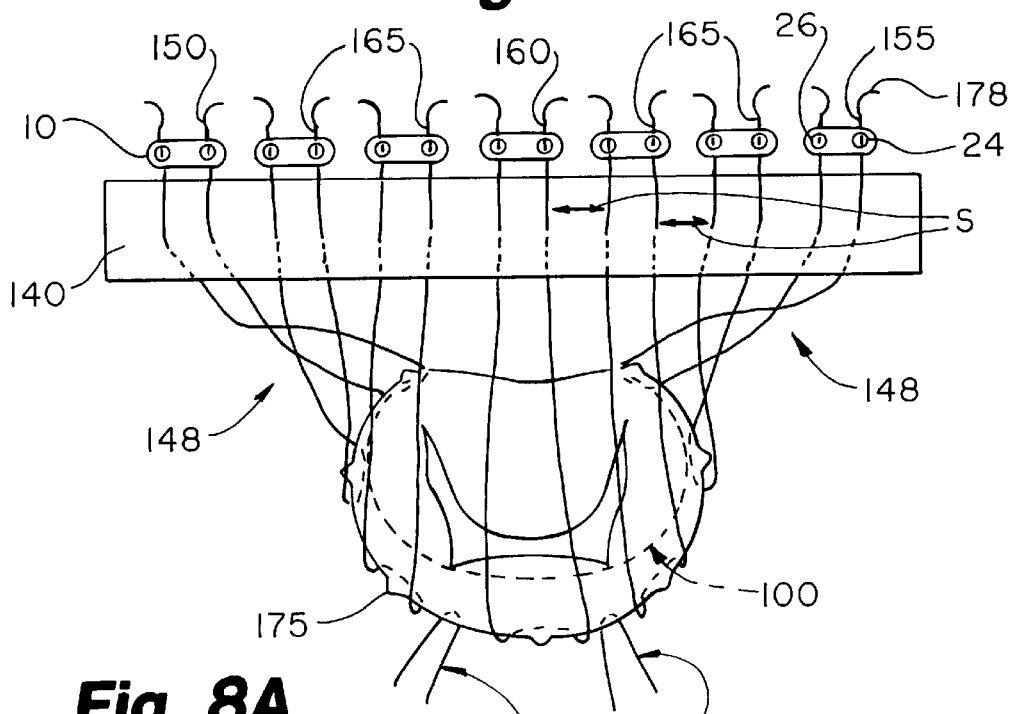
FIG. 7 is a view showing placement of mattress sutures through a pericardial strip and through suture support segments, according to an embodiment of the invention.

Turning to FIG. 7, each mattress suture 148 is then placed near the posterior edge of pericardial strip 140, which is placed shiny side down according to a preferred embodiment. Needles 178 for each suture 148 are passed through strip 140, from the shiny side through the opposite side, and ultimately through segment apertures 24, 26 of each segment 10 as will be described with reference to FIG. 9. The extra width of pericardial strip 140 will be related to mitral orifice 120 after the pericardium is applied to tissue annulus 110.

Segments 10 will cause the two limbs of each suture 148 to be spaced about 3 mm apart, correlating to the precise distance D between suture segment apertures 24, 26 of each segment 10. This prevents plication of pericardial strip 140 when each mattress suture 148 is tied.

Segments 10 will also cause exact, consistent spacing S between each mattress suture 148 along the length of pericardial strip 140. This is facilitated by placing the two trigone sutures first, followed by the one or two sutures related to the midpoint of the posterior annulus. The remainder of the sutures are then easily placed between the previously placed sutures. Further, as will be described, a delivery system according to the invention provides precise intervals between segments 10 for accurate placement without "eyeballing".

Figure 8A:
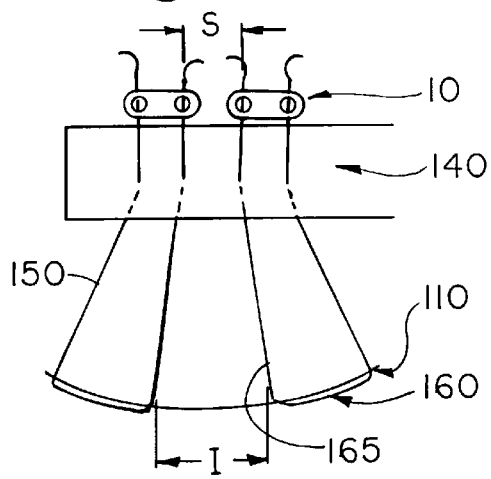
FIGS. 8A–8C are views showing tissue annulus plication beneath and between suture support segments, according to embodiments of the invention.
Figure 8B:
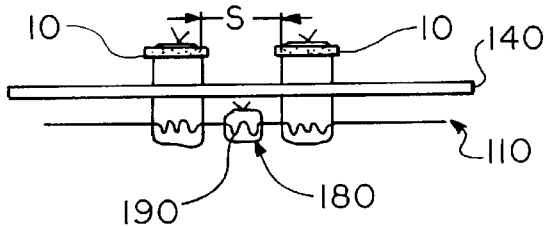

As shown in FIG. 8A, if intervals I between mattress sutures 148 in tissue annulus 110 are greater than spacing intervals S in pericardial strip 140, then compression sutures 180 are used, as shown in FIGS. 7 and 8B, according to one embodiment. Compression sutures 180 are typically of e.g. 2-0 braided polyester and can be placed in a horizontal or a figure-of-8 fashion in tissue annulus 110 to create identical intervals between mattress sutures 148 in both tissue annulus 110 and pericardial strip 140. Of course, other suture sizes and other suture types, such as monofilament sutures, also can be used. FIG. 8B also shows resulting annulus plication 190 between segments 10 and within the loop of compression mattress suture 180. This ensures that the final tissue annulus perimeter dimension is brought precisely to the identical longitudinal dimension of pericardial strip 140.

Figure 8C:
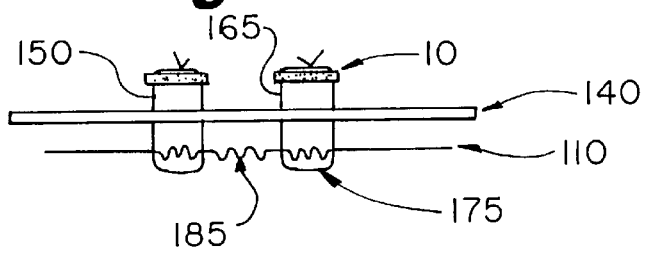

In all cases, the pericardial material of strip 140 between segments 10 will accomplish any residual tissue annulus plication not already accomplished beneath segments 10, as shown for example at 185 in FIG. 8C, by performing a simple tissue annulus advancement with a final running suture (analogous to Carpentier's "sliding leaflet pasty"). This second and final running suture is conceptually different from an initial running annuloplasty suture since the tissue annulus has already been plicated between segments by the pericardium and simply needs to be affixed to it. This will be more reliable with a suture material such as polyamide which has no "memory," rather than polypropylene.

Figure 9:
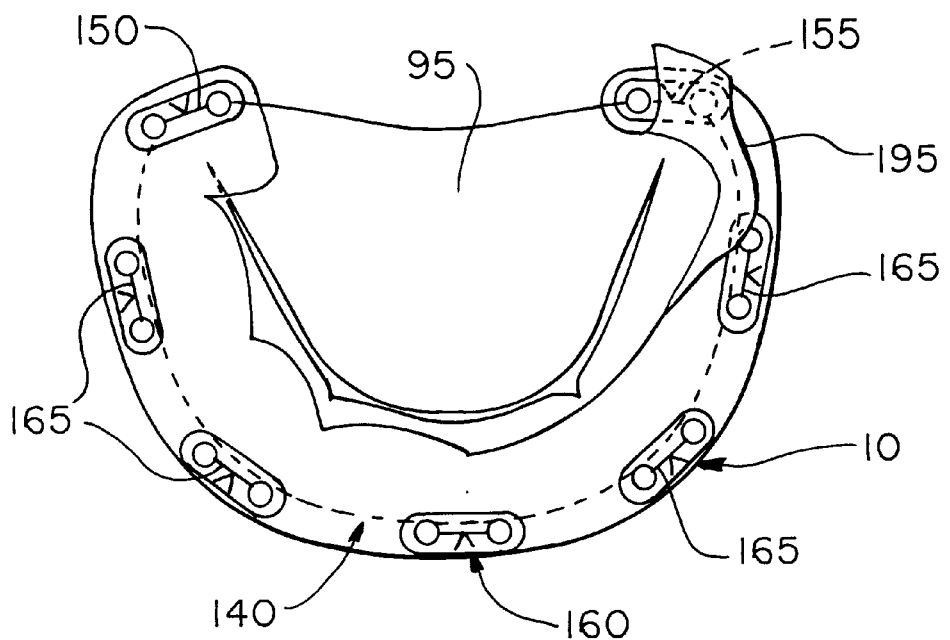
FIG. 9 is a view showing segments tied over pericardium, and pericardium in the process of being folded over the segments to form a tube, completely enclosing the segments over 360 degrees, according to an embodiment of the invention.

At this point in the procedure, as shown in FIG. 9, pericardial strip 140 is pushed down to tissue annulus 110, again shiny side down, so that pericardial strip 140 lies directly on tissue annulus 110. The two limbs of the suture loop of each individual mattress suture 148 are passed through the two segment apertures 24, 26 of each segment 10, and then each segment 10 is also pushed down to pericardial strip 140 so that each segment 10 lies on top of it. Each mattress suture 148 is then tied firmly over each segment 10, and the knot tails cut.

Figure 10:
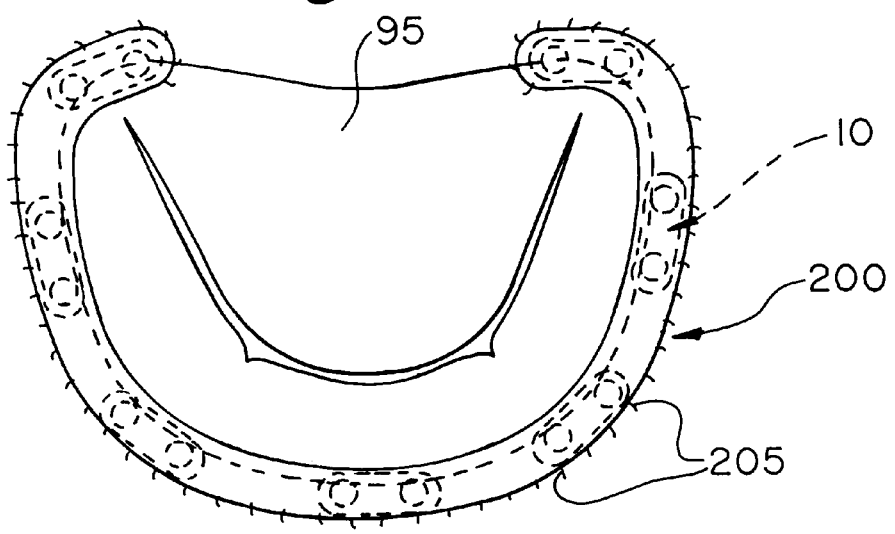
FIG. 10 is a view showing a completed posterior annuloplasty ring constructed of suture support segments and autologous pericardium, the pericardium completely enclosing the segments over 360 degrees to form a tube, according to an embodiment of the invention.

Extra pericardial strip 140 is then folded tightly back from mitral orifice 120, over the top of segments 10 and their knots, as shown beginning at 195 in the FIG. 9 embodiment. The shiny side of the pericardium will then be on top of the smooth folded edge of pericardial strip 140 immediately adjacent to mitral orifice 120. The free edges of the two layers of the pericardial strip 140 will be immediately adjacent to the supra-annular atrial endocardium along the back edges of segments 10. Extra pericardium is then trimmed away at the ends of the two trigonal segments 10 and along the back edge of all segments 10, leaving just enough for a running suture line 205. The folding process creates a two-layer pericardial tube 200, as shown in FIG. 10.

Suture line 205, preferably a shallow-running, non-plicating 5-0 monofilament suture with no "memory" (such as polyamide, which has less tendency to "purse-string" than polypropylene, although polypropylene can be used if carefully applied), sutures tube 200 to the underlying endocardium. More specifically, the top and bottom layers of pericardial tube 200 are thus sutured to the adjacent supra-annular atrial endocardium. Beginning at the trigones 75, 80 with two separate sutures, the suturing process will end at the midpoint of the posterior annulus 110 along the atrial side of pericardial strip 140, according to preferred embodiment. A single suture can also be used. The autologous pericardial annuloplasty ring resulting from the overall process has significant advantages over prior art rings.

The added strength of two layers of pericardium, for example, makes it highly unlikely that a pericardial ring according to embodiments of the invention will stretch. Additionally, pericardial tube 200 completely encloses all of the segments 10 and the suture knots, transforming a plurality of isolated segments 10 and pericardial strip 140 into an integral unit. By anchoring pericardial tube 200 to the atrial endocardium, scarring and pannus formation is minimized, and any risk of a segment 10 dislodging and embolizing is virtually eliminated. Further, with only the shiny side of pericardial tube 200 and three small monofilament suture knots exposed to the tissue annulus and the bloodstream, it is highly likely that annuloplasty rings according to the invention are non-thrombogenic and that Warfarin anticoagulation will not be required. Other advantages are described elsewhere in this application.

A sizing and/or delivery system for possible use with previous embodiments of the invention will now be described, with respect to FIGS. 11–16.

Figure 11:
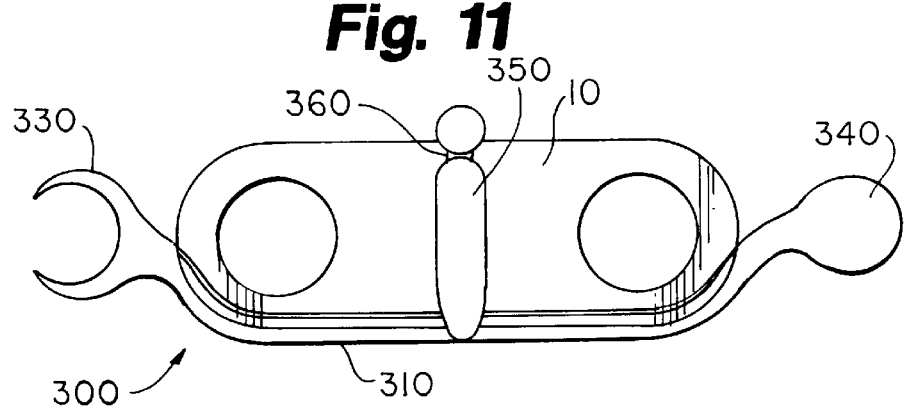
FIG. 11 is a top view of a sizing and delivery system according to an embodiment of the invention.

As shown in FIG. 11, each segment 10 is supported by an element of a segment sizing and/or delivery system 300. The phrase "sizing and/or delivery system" as used herein should be construed to include a system for sizing an anatomical structure and/or for delivering either a single segment 10 or a plurality of segments 10 in either linked-together form or in separated form, as will be described. System 300 includes at least one segment holder 310, as shown in e.g. FIGS. 11–12.

Figure 12A:
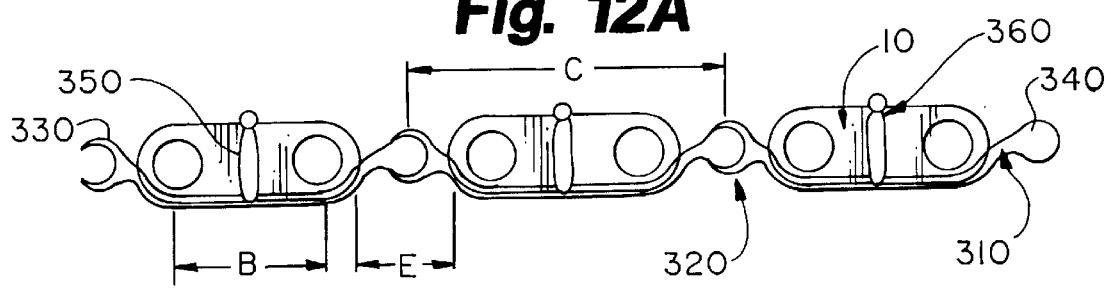
FIG. 12A is a top view of a sizing and delivery system, including a plurality of the elements shown in FIG. 11 linked together, according to an embodiment of the invention.
Figure 12B:
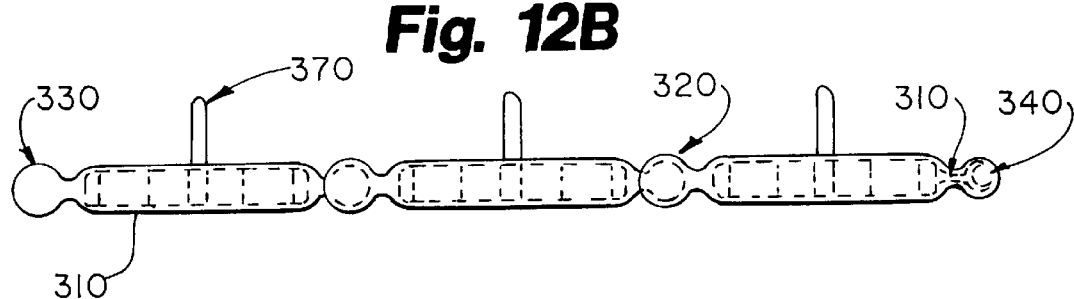
FIG. 12B is a side view of the FIG. 12A system.
Figure 12C:
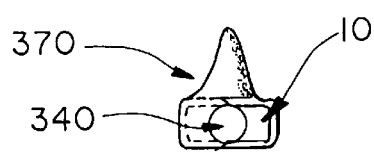
FIGS. 12C–12D are end views of the system shown in FIGS. 12A–12B.

Individual segment holders 310 may be linked together, as shown in e.g. FIGS. 12A–12B, by a series of joints 320. Segment holders 310 can be readily joined together and readily separated at joints 320. The joints 320 illustrated in the figures are universal-type joints, each including a socket member 330 and a ball member 340. Socket member 330 of one holder 310 receives and engages ball member 340 of an adjacent holder 310. Joints 320 thus provide flexibility in substantially all directions, making it easier to accommodate/match a particular valve shape than with standard, rigid, planar, 2-dimensional sizers of the prior art. Additionally, according to a preferred embodiment, joints 320 have sufficient friction, for example by "texturing" the contacting surface of joints 320, to maintain linked-together segment holders 310 in a desired overall shape, while also allowing the above-described flexibility and relative movement between adjacent segment holders 310 to occur. Thus, linked-together segment holders 310 can readily accommodate and maintain the shape of a particular valve morphology.

To promote ready grasping and movement of segment holders 310, each holder 310 preferably includes at least one clamp fin 370. Clamp fins 370 can be easily gripped by clamp 375 (FIG. 13) or similar standard tool, eliminating the need for a specialized holding device or handle. According to one embodiment, clamp fins 370 also have texturing or equivalent structure to provide a better gripping engagement with clamp 375 or other tool.

Adjacent segment holders 310 hold ends of adjacent segments 10 apart by a substantially exact distance E, as shown in FIG. 12A. According to one embodiment, distance E is about 3 mm, providing uniform inter-segment intervals of about 3 mm for implantation of segments 10. To this end, joints 320 are separated by a uniform distance C, which according to one embodiment is about 1 cm. Thus, linked-together segment holders 310 create consistent, uniform, predictable dimensions for precise segment delivery, without the need for ink or suture markings on the ring material. The preferably 1 cm spacing C also encourages surgeons to think of the perimeter of the mitral orifice 120 in meaningful numbers, such that segment holders 310 also lend themselves well to use as a sizing system, with or without a segment delivery aspect.

Each segment holder 310 includes structure for readily releasably holding each suture support segment 10 in place on its respective holder 310. According to a preferred embodiment, this structure includes belt 350, constructed to extend at least partially around a respective segment 10. Belt 350 of each segment holder 310 is preferably disposed at a predetermined location between opposite ends of holder 310, i.e. between joints 320, providing a convenient visual reference for the surgeon. In the illustrated embodiment, belt 350 is disposed exactly halfway between joints 320, but of course other placements of belt 350 are contemplated. Additionally, according to an alternative embodiment, one or two belts can extend through apertures 24, 26. By extending through the back ends of apertures 24, 26 and not extending entirely around the full width of the segment, the mattress suture can be tied tight before the segment is disengaged from its holder. A belt 350 wrapped entirely around segment 10 at the middle of holder 310, on the other hand, would prevent the suture from lying flat against segment 10.

Figure 12D:
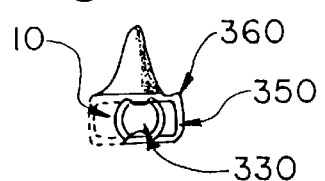

Each belt 350 preferably includes separation notch 360, which allows belt 350 easily to be cut for removal of segment 10 from segment holder 310. As shown in FIG. 12D, separation notch 360 is preferably disposed near clamp fin 370, for easy access by the surgeon and so that fin 370 can be used as a guide to locate notch 360 if needed. Of course, other locations for notch 360, and the use of multiple notches 360, are also contemplated.

Segment holders 310 can be made of any suitable material that is preferably inert, non-corrosive, non-thrombogenic and biocompatible with blood and tissue. Segment holders 310 can be formed of a plastic material according to a disposable, non-reusable embodiment, for example. For use solely as a sizing system, as will be described, i.e. in a non-disposable, reuseable embodiment, elements 310 can be formed of titanium, for example.

Figure 13:
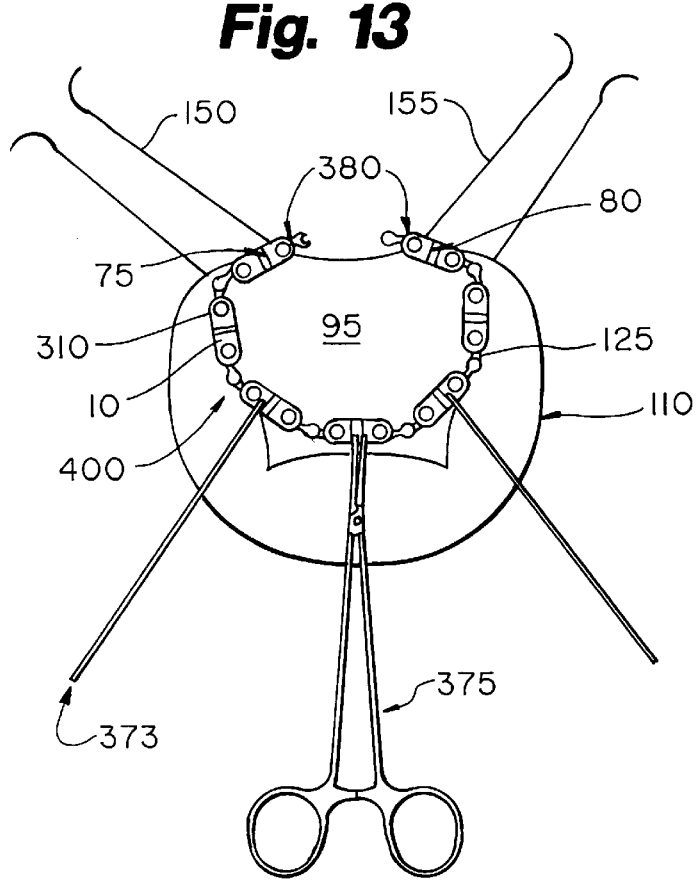
FIG. 13 is a view showing placement of a sizing and delivery system on the perimeter of an unfurled anterior leaflet, according to an embodiment of the invention.
Figure 14:
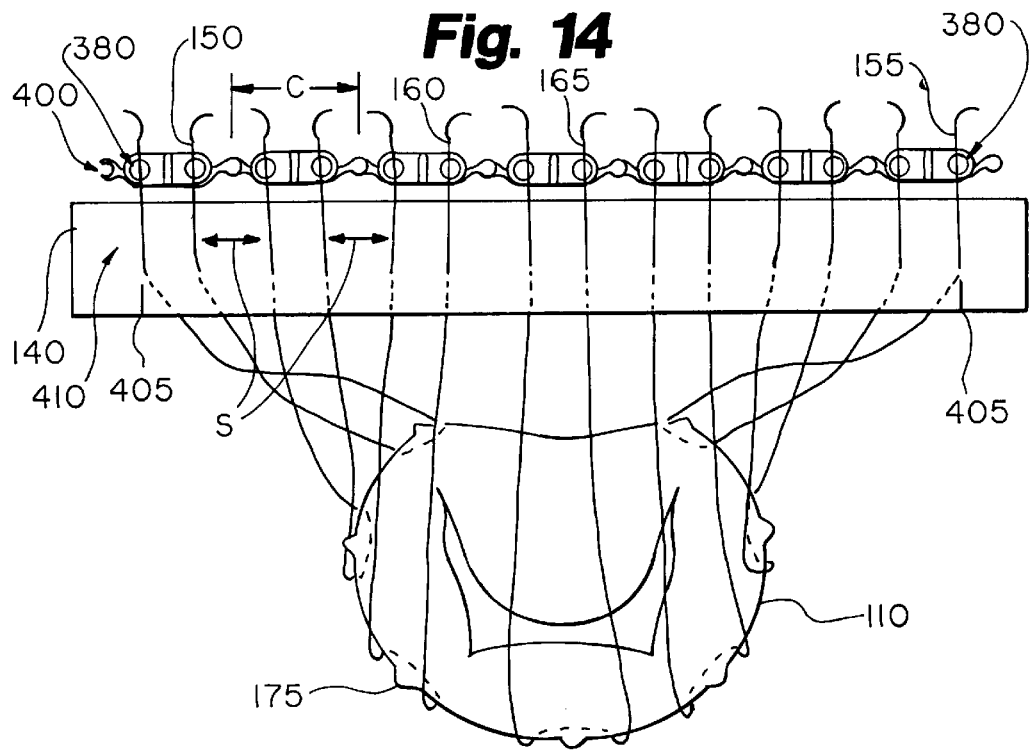
FIG. 14 is a view showing placement of mattress sutures in ring material and segments using a sizing and delivery system according to an embodiment of the invention.

Turning to FIGS. 13–14, linked-together line 400 of segments 10 and segment holders 310 is used to measure perimeter dimension 125 of anterior mitral leaflet 95, along the long axis of each segment 10. Leaflet 95 is unfurled using hook 373 pulling chordae tendineae, for example, although other equivalent means are also contemplated. Apertures 24, 26 in each segment 10 and universal joints 320 are used as a guide in the measuring process. Line 400 can measure dimension 125 with high accuracy and precision; for that matter, line 400 can accurately and precisely measure other reference dimensions, for example the perimeter of two fingers or of a generic valve sizer.

The precise perimeter dimension 125 of anterior mitral leaflet 95 for posterior annuloplasty is measured preferably by using the minimum number of segments 10 required to "catch" the fibrous trigones 75, 80 with the last sutures 150, 155 on each end of what eventually will become pericardial tube 200. Any extra length of ring material required, by adding another segment 10 during the measurement, can be added medially to each of the fibrous trigones 75, 80 along anterior annulus 90. This ensures absolute precision at the time of the perimeter dimension measurement 125 along the free edge of anterior mitral leaflet 95, and that both trigones 85, 90 are "hooked" in every case. In other words, any extra length of ring material is allowed to slightly overlap each of trigones 75, 80. No anterior annulus tissue medial to fibrous trigones 75, 80 need be plicated and, according to a preferred embodiment, such tissue is typically never plicated.

Precise perimeter dimensions for a complete ring are accomplished by using the minimum number of linked segments required to cover the entire perimeter along the anterior annulus without overlapping. Additionally, for a complete ring, any gap between segments is placed in the middle of the anterior annulus and will be covered with ring material.

Turning to FIG. 14, for both posterior and complete rings, end sutures 150, 155 are placed first in tissue annulus 110 exactly where delivery system 300 indicates, at the location of the end holes 380, to ensure a precise measurement. The appropriately sized delivery system 300 is then straightened and placed just above the ring material, in a manner similar to that described with reference to FIG. 7.

The outside limbs of end sutures 150, 155 are then placed at the outer extremities of ring material 140, leaving enough ring material to cover segments 10 with a final running suture. In FIG. 14, 405 represents the precise end of the ring material involved in tissue annulus plication, and 410 represents additional ring material used to enclose the segments 10. Once end sutures 150, 155 are placed, remaining sutures 160, 165 are simply brought up through ring material 140 and through segment apertures 24, 26, exactly as segments 10 present themselves in segment holders 310. This eliminates any guesswork or "eyeballing" on the part of the surgeon, guaranteeing precise intervals not only within the suture loops (spacing D, FIG. 1B) of sutures 148, but also between segments (spacing E, FIG. 12A, spacing S, FIG. 14) in ring material 140. The precise, repeatable intervals between sutures 148, as well as the precise, repeatable spacing within the sutures loops, present significant advantages, as will be apparent to those of ordinary skill in the art.

Ring material 140 and segments 10 are then transferred down to the tissue annulus, as with the previously described embodiments. Preferably thereafter, each segment holder 310 is separated from its respective segment 10 by severing belt or belts 350 at separation notch 360, as described earlier. The entire group of linked segment holders 310 is released from segments 10 preferably, although not necessarily, as a unit. Segment holders 310 are probably best released from segments 10 after ring material 140 and segments 10 are applied to the tissue annulus, and before the sutures are tied, but of course alternative release timing is also contemplated according to the invention.

As shown in FIG. 15, segments 10 and holders 310 can be sold individually, to be added together to accommodate any and all unique anterior mitral or tricuspid leaflet sizes, satisfying surgeons who operate with the paradigm of precision (e.g. Carpentier, Cosgrove). Each individual segment 10 and its corresponding segment holder 310 are enclosed within shell 420, which preferably is formed of hard, clear plastic or equivalent material. Within each shell 420 is an underlying cloth material 425, for example a purple velvet pillow or other material designed to provide desired support and aesthetic characteristics.

Alternatively, as shown in FIG. 16, segments 10 and segment holders 310 can be sold together as a standard partial or complete ring to satisfy surgeons who operate under a "one ring size for all patients" paradigm (e.g. Cooley, Orsulak). FIG. 16 shows a line 400 of linked-together segment holders 310 enclosed within a single shell 420. Shell 420 preferably is in the approximate shape of the mitral or tricuspid orifice, to reduce the amount of shaping that must be performed by the surgeon. Underlying cloth material 425 is also used.

Thus, the packaging material according to the invention can encase each of the plurality of segment holders individually, or the plurality of segment holders collectively.

It should be noted that the sizing aspects of delivery system 300 can be used independently of or in connection with the segment delivery aspects of system 300. In this regard, segment holders 310 may also be viewed as sizing elements, useable both with and without associated segments 10. FIGS. 12A–12D illustrate an embodiment in which sizing elements 310 are used with segments 10; FIGS. 17–18 illustrate embodiments in which sizing elements 310 are used without segments 10.

FIG. 17 is a side view which basically shows the embodiment of FIG. 12B, with segments 10 eliminated. FIG. 18 is a top view and is similar to FIG. 12A, with segments eliminated and with sizing elements 310 separated slightly. Each illustrated sizing element 310' comprises a substantially straight, substantially cylindrical member with interlocking, e.g. snap-fitting, male and female ends 340', 330' which are substantially identical to those of FIGS. 12A–12B. The joints preferably are identical, whether the sizing element is used with or without segments. Belt 350 preferably is eliminated in the embodiment of FIGS. 17–18, due to the absence of segments 10. Additionally, clamp fins 370 are optional in these embodiments and, for that matter, in the embodiment of FIGS. 12A–12D.

Each sizing element 310 is preferably of a known uniform length, e.g. 1 cm, and includes linking structure, e.g. joints 320, for linking a number of sizing elements together. By knowing the uniform length of each sizing element 310, and by counting the number of sizing elements 310 needed to traverse a particular perimeter or other dimension, the surgeon can easily determine the length of a desired anatomical structure or other object. Of course, the sizing aspects of system 310 work very well with the segment delivery aspects, as described herein.

It should also be noted that embodiments according to the invention are well-suited for minimally invasive surgery. Line 400 of segments 10 and/or segment holders or sizing elements 310 can be fed in a snake-like fashion through a surgical opening of minimal size ("port-access"), and the valve-sizing, -stabilizing and/or circumference-reducing functions carried out accordingly. This represents another significant advantage over the typical annuloplasty ring and sizer, which generally require a substantially larger surgical opening.

In view of the foregoing description, those of ordinary skill will recognize the above and other significant advantages of the invention in its various embodiments. Precise measurement of each unique anterior mitral or tricuspid leaflet is possible. The linked-together segment holders 310 constitute a universal sizer and/or delivery system, useable to determine the unique size of, precisely stabilize, and/or precisely reduce the circumference of a wide variety of anatomical structures. Precise, customized annuloplasty, for example, is possible for every patient.

Embodiments according to the invention also promote the number of choices available to the surgeon, increasing the attractiveness of the invention to surgeons who are used to working within particular surgical paradigms. For example, surgeons can choose their own ring material, can choose to do either a partial or complete annuloplasty without having to obtain and alter current annuloplasty rings, and can follow a "one-size-fits-all" surgical approach or a more customized approach, as described above.

According to the invention, a prescribed number of mattress sutures is determined from the anterior mitral or tricuspid leaflet perimeter measurement and is easily visualized with the disclosed sizer/segment delivery system. The mattress sutures are preferably evenly spaced and purposely separated from each other in the tissue annulus, rather than abutted immediately next to each other. Additionally, the mattress sutures are placed at precise repeating intervals along the entire length of the ring material, facilitated by the segment delivery system.

The universal sizer aspects of the invention allow surgeons to relate to the circumference of the mitral or tricuspid orifice by directly measuring the perimeter of the anterior mitral or tricuspid leaflet in centimeters, instead of by indirect measurements of intertrigonal or intercommissural dimensions, anterior leaflet height dimensions, or transverse mitral or tricuspid orifice diameters.

A segment of only one size, which can be linked by the delivery system to any number of other segments, eliminates the need for inventories of multiple sizes of annuloplasty rings and of rings for both mitral and tricuspid valves, for example. Additionally, inventories of multiple sizers are unnecessary since the segment delivery system is also a universal sizer for either the mitral or tricuspid valves, for example. The sizer is universally flexible and is adjusted by adding or subtracting segments via the segment delivery system.

If untreated viable autologous pericardium can be reliably used as ring material, Warfarin anticoagulation is probably completely unnecessary for any time interval. Scar and pannus formation is minimized, eliminating the need for any tissue ingrowth as an autologous pericardial tube is firmly attached to the annulus and completely encloses the segments and their suture knots. Non-thrombogenicity would then be virtually guaranteed, because the pericardial tube, shiny side (mesothelial surface) out, is firmly attached to the annulus and completely encloses the segments and their suture knots.

The invention should not be considered limited to the specific methods and devices precisely described herein. On the contrary, various modifications will be apparent to those of ordinary skill upon reading this disclosure. For example, the consistent, uniform inter-segment intervals can be construed to be divided into sets of intervals of different lengths, for example 3 mm between certain segments and 5 mm between certain other segments, to suit a particular procedure or pathology. The terms perimeter and circumference as used herein should also be construed to refer to either a complete ring or a partial ring, again to suit a particular application. Although certain embodiments are described with reference to mitral valves and/or both mitral and tricuspid valves, use with other valves or anatomical structures are also contemplated. Additionally, the segment holders/sizing elements according to the invention can be made of disposable material, for one-time use, or of non-disposable material, for re-sterilization and subsequent reuse. Other modifications will be apparent to those of ordinary skill.

What is claimed is:

1. A delivery system for delivering a plurality of substantially rigid suture support segments during a surgical procedure, the substantially rigid suture support segments to be placed at least partially circumferentially about an anatomical structure to form a line of discrete suture support segments for at least stabilizing the anatomical structure along the line of discrete suture support segments, the delivery system comprising a plurality of segment holders, the plurality of segment holders being readily releasably securable to the plurality of substantially rigid suture support segments and separating the plurality of substantially rigid suture support segments from each other.

2. The delivery system of claim 1, wherein the plurality of segment holders comprise linking structure to link the segment holders together.

3. The delivery system of claim 2, wherein the segment holders, when linked together, define consistent dimensions to precisely size an anatomical vascular structure.

4. The delivery system of claim 2, wherein the segment holders, when linked together, define consistent intervals for delivering the suture support segments to an anatomical vascular structure.

5. The delivery system of claim 2, wherein the linking structure is constructed to allow a desired number of segment holders to be linked together to fit a particular anatomical structure.

6. The delivery system of claim 2, wherein the linking structure comprises a plurality of universal joints connecting adjacent segment holders together.

7. The delivery system of claim 2, wherein the linking structure comprises a plurality of ball-and-socket joints connecting adjacent segment holders together.

8. The delivery system of claim 2, wherein the linking structure comprises a plurality of joints connecting adjacent segment holders together, the joints having sufficient friction to maintain linked-together segment holders in a desired overall shape but allowing relative movement between adjacent segment holders.

9. The delivery system of claim 1, wherein each segment holder readily releasably secures exactly one substantially rigid support segment.

10. The delivery system of claim 1, wherein each segment holder comprises at least one belt constructed to extend at least partially around a respective suture support segment to readily releasably secure the suture support segment to the segment holder.

11. The delivery system of claim 10, wherein each segment holder comprises opposite ends, further wherein the at least one belt of each segment holder is disposed at a predetermined location between the opposite ends to provide a visual reference point.

12. The delivery system of claim 10, wherein the at least one belt of each segment extends through at least one aperture of the suture support segment.

13. The delivery system of claim 10, wherein the at least one belt defines a separation notch, the belt being severable at the separation notch to separate the suture support segment from the segment holder.

14. The delivery system of claim 1, wherein each segment holder comprises a clamp fin, the clamp fin being constructed for ready grasping to allow easy relocation of the segment holder.

15. The delivery system of claim 1, further comprising a packaging material, the packaging material encasing each of the plurality of segment holders individually.

16. The delivery system of claim 1, further comprising a packaging material, the packaging material encasing the plurality of segment holders collectively.

17. The delivery system of claim 16, wherein the packaging material is substantially in the shape of the mitral or tricuspid orifice of a human heart.

18. A sizing system for measuring an anatomical structure during a surgical procedure, the sizing system comprising a plurality of discrete sizing elements, each sizing element being of a known substantially uniform length, the plurality of sizing elements including linking structure to link the sizing elements together, the linking structure having sufficient friction to maintain linked-together sizing elements in a desired overall shape but allowing relative movement between adjacent sizing elements to accommodate the particular shape of the anatomical structure, the sizing elements being constructed for placement generally along the anatomical structure to be measured.

19. The sizing system of claim 18, wherein the sizing elements are segment holders, the sizing system further comprising a plurality of substantially rigid suture support segments to be placed at least partially circumferentially about an anatomical structure to form a line of suture support segments to at least stabilize the anatomical structure along the line of suture support segments, the suture support segments being readily releasably secured to the segment holders.

20. The sizing system of claim 19, wherein the suture support segments have opposite ends, the sizing elements supporting facing ends of adjacent suture support segments about 3 mm apart.

21. The sizing system of claim 18, wherein the linking structure comprises a plurality of joints connecting adjacent sizing elements together, the joints being spaced about 1 cm apart.

22. The sizing system of claim 18, wherein the linking structure comprises a plurality of universal joints connecting adjacent sizing elements together.

23. The sizing system of claim 18, wherein each sizing element comprises a clamp fin, the clamp fin being constructed for ready grasping to allow easy relocation of the sizing element.

24. A sizing and delivery system for use in a surgical procedure on the heart of a patient, the sizing and delivery system comprising:

segment means for reducing the circumference of a heart valve, the segment means comprising a plurality of substantially rigid, substantially identical suture support segments, the suture support segments having aperture means therethrough for receiving sutures, the segment means being constructed for placement at least partially circumferentially about the heart valve to form a line of discrete suture support segments for reducing the circumference of and stabilizing the heart valve along the line of discrete suture support segments; and segment holding means for releasably holding the segment means during delivery of the segment means to the heart during the surgical procedure, the segment holding means comprising a plurality of substantially identical segment holders that are readily releasably securable to the plurality of substantially rigid suture support segments, the segment holders each including linking means for connecting adjacent segment holders together;

wherein:

a desired number of segment holders can be linked together by linking structure to form a chain of linked segment holders of a desired length, corresponding to the size of the heart valve of the patient, the linking structure having sufficient friction to maintain the linked-together segment holders in a desired overall shape but allowing relative movement between adjacent segment holders to accommodate the particular shape of the heart valve of the patient;

the segment holders are each discrete sizing elements of a known, substantially uniform length for precise valve sizing, the sizing elements being constructed for placement generally along the heart valve of the patient; and the segment holders maintain each suture support segment a known distance from an adjacent suture support segment, creating substantially uniform intervals for implantation of the suture support segments.

25. The sizing and delivery system of claim 24, wherein the segment holders are each about 1 cm long.

26. The sizing and delivery system of claim 24, wherein the segment holders maintain each suture support segment about 3 mm from an adjacent suture support segment, creating uniform intervals of about 3 mm for implantation of the suture support segments.

27. The sizing and delivery system of claim 24, further comprising belt means for readily releasably securing the segment means to the segment holding means.

28. The sizing and delivery system of claim 27, wherein the belt means comprises separation notch means for allowing the belt means to be readily severed to release the segment means from the segment holding means.

29. A method of measuring an anatomical structure during a surgical procedure, the method comprising:

(a) placing, during the surgical procedure, a sizing system generally along an anatomical structure to be measured, the sizing system comprising a plurality of discrete sizing elements of known substantially uniform length, the plurality of sizing elements including linking structure to link the sizing elements together;

(b) maintaining the linked-together sizing elements in a desired overall shape, due at least in part to friction of the linking structure;

(c) accommodating the particular shape of the anatomical structure by allowing relative movement between adjacent sizing elements with the linking structure; and (d) determining the perimeter of the anatomical structure based on the number of sizing elements needed to extend along an entire desired portion of the anatomical structure.

30. The method of claim 29, further comprising:

(e) using the sizing system to maintain a plurality of discrete, substantially rigid suture support segments at consistent intervals;

(f) suturing the suture support segments into fixed relationship with the anatomical structure at the consistent intervals maintained by the sizing system, the suture support segments being disposed in a line of suture support segments for at least stabilizing the anatomical structure along the line of suture support segments.

31. The method of claim 30, further comprising:

(g) releasing the plurality of suture support segments from the plurality of sizing elements.

32. The method of claim 29, wherein step (a) includes placing the sizing system along the perimeter of an unfurled anterior leaflet of a mitral or tricuspid heart valve, and step (d) includes determining the perimeter of the unfurled anterior leaflet.

33. The method of claim 32, further comprising:

(e) using the sizing system to maintain a plurality of discrete, substantially rigid suture support segments at consistent intervals; and (f) suturing the suture support segments into fixed relationship with a posterior mitral annulus or a posterior and anterior tricuspid annulus at the consistent intervals maintained by the sizing system to bring the circumference of the posterior mitral annulus or posterior and anterior tricuspid annulus into correlation with the perimeter of the unfurled anterior leaflet.

34. The method of claim 33, wherein step (f) includes leaving the anterior mitral annulus or the septal tricuspid annulus free of sutures.

35. The method of claim 32, wherein the method further includes enclosing the support segments within an autologous pericardium ring that is sutured onto the posterior mitral or posterior and anterior tricuspid annulus.

36. A delivery system for delivering a plurality of substantially rigid suture support segments during a surgical procedure, the substantially rigid suture support segments to be placed at least partially circumferentially about an anatomical structure to form a line of discrete suture support segments for at least stabilizing the anatomical structure along the line of discrete suture support segments, the delivery system comprising a plurality of segment holders, the plurality of segment holders being readily releasably securable to the plurality of substantially rigid suture support segments, the plurality of segment holders comprising linking structure to link the segment holders together, the linking structure comprising a plurality of joints connecting adjacent segment holders together, the joints having sufficient friction to maintain linked-together segment holders in a desired overall shape but allowing relative movement between adjacent segment holders.

37. A delivery system for delivering a plurality of substantially rigid suture support segments during a surgical procedure, the substantially rigid suture support segments to be placed at least partially circumferentially about an anatomical structure to form a line of discrete suture support segments for at least stabilizing the anatomical structure along the line of discrete suture support segments, the delivery system comprising a plurality of segment holders, the plurality of segment holders being readily releasably securable to the plurality of substantially rigid suture support segments, wherein each segment holder readily releasably secures exactly one substantially rigid support segment.

38. A delivery system for delivering a plurality of substantially rigid suture support segments during a surgical procedure, the substantially rigid suture support segments to be placed at least partially circumferentially about an anatomical structure to form a line of discrete suture support segments for at least stabilizing the anatomical structure along the line of discrete suture support segments, the delivery system comprising a plurality of segment holders, the plurality of segment holders being readily releasably securable to the plurality of substantially rigid suture support segments, wherein each segment holder comprises a clamp fin, the clamp fin being constructed for ready grasping to allow easy relocation of the segment holder.

39. A delivery system for delivering a plurality of substantially rigid suture support segments during a surgical procedure, the substantially rigid suture support segments to be placed at least partially circumferentially about an anatomical structure to form a line of discrete suture support segments for at least stabilizing the anatomical structure along the line of discrete suture support segments, the delivery system comprising a plurality of segment holders, the plurality of segment holders constructed to be released from the plurality of substantially rigid suture support segments once the suture support segments are delivered to the anatomical structure, the suture support segments being constructed to remain at the anatomical structure after delivery and the plurality of segment holders being constructed for complete removal from the anatomical structure after delivery.

40. A delivery system for delivering a plurality of substantially rigid suture support segments during a surgical procedure, the substantially rigid suture support segments to be placed at least partially circumferentially about an anatomical structure to form a line of discrete suture support segments for directly supporting sutures extending into the anatomical structure and for at least stabilizing the anatomical structure along the line of discrete suture support segments, the delivery system comprising a plurality of segment holders, the plurality of segment holders being readily releasably securable to the plurality of substantially rigid suture support segments, the plurality of segment holders being distinct from the sutures.

* * * * *